United States Patent
Purkayastha et al.

(10) Patent No.: US 12,016,355 B2
(45) Date of Patent: Jun. 25, 2024

(54) STEVIA COMPOSITION

(71) Applicant: PURECIRCLE SDN BHD, Kuala Lumpur (MY)

(72) Inventors: Siddhartha Purkayastha, Chicago, IL (US); Avetik Markosyan, Yerevan (AM); Marquita Johnson, Oak Lawn, IL (US); Monica Moralma Garces Ortega, Westmont, IL (US)

(73) Assignee: PURECIRCLE SDN BHD, Kuala Lumpur (MY)

( * ) Notice: Subject to any disclaimer, the term of this patent is extended or adjusted under 35 U.S.C. 154(b) by 240 days.

(21) Appl. No.: 17/118,702

(22) Filed: Dec. 11, 2020

(65) Prior Publication Data

US 2021/0092979 A1 Apr. 1, 2021

Related U.S. Application Data

(60) Continuation of application No. 16/695,137, filed on Nov. 25, 2019, now abandoned, which is a continuation of application No. 15/373,429, filed on Dec. 8, 2016, now Pat. No. 10,485,249, which is a division of application No. 14/123,684, filed as application No. PCT/US2012/043294 on Jun. 20, 2012, now abandoned, said application No. 15/373,429 is a continuation-in-part of application No. 13/129,158, filed as application No. PCT/US2011/036063 on May 11, 2011, now Pat. No. 10,362,797.

(60) Provisional application No. 61/531,802, filed on Sep. 7, 2011, provisional application No. 61/499,171, filed on Jun. 20, 2011, provisional application No. 61/441,443, filed on Feb. 10, 2011.

(51) Int. Cl.
| | |
|---|---|
| A23L 2/60 | (2006.01) |
| A23L 27/30 | (2016.01) |
| A23L 33/10 | (2016.01) |
| A61K 8/60 | (2006.01) |
| A61Q 11/00 | (2006.01) |

(52) U.S. Cl.
CPC ............. *A23L 2/60* (2013.01); *A23L 27/33* (2016.08); *A23L 27/34* (2016.08); *A23L 27/36* (2016.08); *A23L 33/10* (2016.08); *A61K 8/602* (2013.01); *A61Q 11/00* (2013.01); *A23V 2002/00* (2013.01); *A61K 2800/40* (2013.01)

(58) Field of Classification Search
CPC . A23L 2/60; A23L 33/10; A23L 27/33; A23L 27/34; A23L 27/36; A61K 8/602; A61K 2800/40; A61Q 11/00; A23V 2002/00
See application file for complete search history.

(56) References Cited

U.S. PATENT DOCUMENTS

| | | |
|---|---|---|
| 3,723,410 A | 3/1973 | Persinos |
| 4,082,858 A | 4/1978 | Morita et al. |
| 4,171,430 A | 10/1979 | Matsushita et al. |
| 4,219,571 A | 8/1980 | Miyake |
| 4,353,889 A | 10/1982 | Dubois |
| 4,361,697 A | 11/1982 | Dobberstein et al. |
| 4,454,290 A | 6/1984 | Dubois |
| 4,590,160 A | 5/1986 | Nishihashi et al. |
| 4,599,403 A | 7/1986 | Kumar |
| 4,612,942 A | 9/1986 | Dobberstein et al. |
| 4,657,638 A | 4/1987 | Le Grand et al. |
| 4,892,938 A | 1/1990 | Giovanetto |
| 4,917,916 A | 4/1990 | Hirao et al. |
| 5,112,610 A | 5/1992 | Kienle |
| 5,576,042 A | 11/1996 | Fuisz |
| 5,779,805 A | 7/1998 | Morano |
| 5,962,678 A | 10/1999 | Payzant et al. |
| 5,972,120 A | 10/1999 | Kutowy et al. |
| 6,031,157 A | 2/2000 | Morita et al. |
| 6,080,561 A | 6/2000 | Morita et al. |
| 6,204,377 B1 | 3/2001 | Nishimoto et al. |
| 6,228,996 B1 | 5/2001 | Zhou et al. |
| 6,706,304 B1 | 3/2004 | Ishida et al. |
| 7,807,206 B2 | 10/2010 | Magomet et al. |
| 7,838,011 B2 | 11/2010 | Abelyan et al. |
| 7,838,044 B2 | 11/2010 | Abelyan et al. |
| 7,862,845 B2 | 1/2011 | Magomet et al. |
| 8,257,948 B1 | 9/2012 | Markosyan |
| 10,362,797 B2 | 7/2019 | Markosyan |
| 10,485,249 B2 | 11/2019 | Purkayastha et al. |
| 2002/0132320 A1 | 9/2002 | Wang et al. |
| 2003/0161876 A1 | 8/2003 | Hansson et al. |
| 2003/0236399 A1 | 12/2003 | Zheng et al. |

(Continued)

FOREIGN PATENT DOCUMENTS

| | | |
|---|---|---|
| BR | P10701736 | 7/2008 |
| CN | 1049666 | 3/1991 |

(Continued)

OTHER PUBLICATIONS

"Acetone". Available online from Sigma-Aldrich as of Jan. 4, 2016. pp. 1-2.

(Continued)

*Primary Examiner* — Michael P Cohen

(74) *Attorney, Agent, or Firm* — Rachael Casey

(57) ABSTRACT

*Stevia* compositions are prepared from steviol glycosides of *Stevia rebaudiana* Bertoni. The compositions are able to provide a superior taste profile and can be used as sweetness enhancers, flavor enhancers and sweeteners in foods, beverages, cosmetics and pharmaceuticals.

6 Claims, 7 Drawing Sheets

(56) References Cited

U.S. PATENT DOCUMENTS

| | | |
|---|---|---|
| 2006/0083838 A1 | 4/2006 | Jackson et al. |
| 2006/0134292 A1 | 6/2006 | Abelyan et al. |
| 2006/0142555 A1 | 6/2006 | Jonnala et al. |
| 2007/0082102 A1 | 4/2007 | Magomet et al. |
| 2007/0082103 A1 | 4/2007 | Magomet et al. |
| 2007/0116800 A1 | 5/2007 | Prakash et al. |
| 2007/0116819 A1 | 5/2007 | Prakash et al. |
| 2007/0116820 A1 | 5/2007 | Prakash et al. |
| 2007/0116821 A1 | 5/2007 | Prakash et al. |
| 2007/0116822 A1 | 5/2007 | Prakash et al. |
| 2007/0116823 A1 | 5/2007 | Prakash et al. |
| 2007/0116824 A1 | 5/2007 | Prakash et al. |
| 2007/0116825 A1* | 5/2007 | Prakash .......... A23G 4/06 426/660 |
| 2007/0116826 A1 | 5/2007 | Prakash et al. |
| 2007/0116827 A1 | 5/2007 | Prakash et al. |
| 2007/0116828 A1 | 5/2007 | Prakash |
| 2007/0116829 A1 | 5/2007 | Prakash et al. |
| 2007/0116830 A1* | 5/2007 | Prakash .......... A23C 9/156 426/548 |
| 2007/0116831 A1 | 5/2007 | Prakash et al. |
| 2007/0116832 A1 | 5/2007 | Prakash et al. |
| 2007/0116833 A1 | 5/2007 | Prakash et al. |
| 2007/0116834 A1 | 5/2007 | Prakash et al. |
| 2007/0116835 A1 | 5/2007 | Prakash et al. |
| 2007/0116836 A1 | 5/2007 | Prakash et al. |
| 2007/0116837 A1 | 5/2007 | Prakash et al. |
| 2007/0116838 A1 | 5/2007 | Prakash et al. |
| 2007/0116839 A1 | 5/2007 | Prakash et al. |
| 2007/0116840 A1 | 5/2007 | Prakash et al. |
| 2007/0116841 A1 | 5/2007 | Prakash et al. |
| 2007/0128311 A1 | 6/2007 | Prakash et al. |
| 2007/0134390 A1 | 6/2007 | Prakash et al. |
| 2007/0134391 A1 | 6/2007 | Prakash et al. |
| 2007/0224321 A1 | 9/2007 | Prakash et al. |
| 2007/0292582 A1 | 12/2007 | Prakash et al. |
| 2008/0064063 A1 | 3/2008 | Brandle et al. |
| 2008/0102497 A1 | 5/2008 | Wong et al. |
| 2008/0107775 A1 | 5/2008 | Prakash et al. |
| 2008/0107776 A1 | 5/2008 | Prakash et al. |
| 2008/0107787 A1 | 5/2008 | Prakash et al. |
| 2008/0108710 A1 | 5/2008 | Prakash et al. |
| 2008/0111269 A1 | 5/2008 | Politi et al. |
| 2008/0226770 A1 | 9/2008 | Lee et al. |
| 2008/0226797 A1 | 9/2008 | Lee et al. |
| 2008/0292764 A1 | 11/2008 | Prakash et al. |
| 2008/0292765 A1 | 11/2008 | Prakash et al. |
| 2008/0292775 A1 | 11/2008 | Prakash et al. |
| 2008/0300402 A1 | 12/2008 | Yang et al. |
| 2009/0017185 A1 | 1/2009 | Catani |
| 2009/0053378 A1 | 2/2009 | Prakash et al. |
| 2009/0074935 A1 | 3/2009 | Lee |
| 2009/0079935 A1 | 3/2009 | Harris et al. |
| 2009/0142817 A1 | 6/2009 | Norman et al. |
| 2009/0226590 A1 | 9/2009 | Fouache et al. |
| 2010/0055752 A1 | 3/2010 | Kumar |
| 2010/0056472 A1 | 3/2010 | Duan et al. |
| 2010/0099857 A1 | 4/2010 | Evans et al. |
| 2010/0011215 A1 | 5/2010 | Abelyan et al. |
| 2010/0057024 A1 | 5/2010 | Cavallini et al. |
| 2010/0120710 A1 | 5/2010 | Watanabe et al. |
| 2010/0013756 A1 | 6/2010 | Prakash et al. |
| 2010/0018986 A1 | 7/2010 | Abelyan et al. |
| 2010/0189861 A1 | 7/2010 | Abelyan et al. |
| 2010/0227034 A1 | 9/2010 | Purkayastha et al. |
| 2010/0255171 A1 | 10/2010 | Purkayastha et al. |
| 2010/0278993 A1 | 11/2010 | Prakash et al. |
| 2010/0285201 A1 | 11/2010 | Catani et al. |
| 2010/0316782 A1 | 12/2010 | Shi et al. |
| 2011/0030457 A1 | 2/2011 | Valery et al. |
| 2011/0033525 A1 | 2/2011 | Liu |
| 2011/0092684 A1 | 4/2011 | Abelyan et al. |
| 2011/0104353 A1 | 5/2011 | Lee |
| 2011/0111115 A1 | 5/2011 | Shi et al. |
| 2011/0123677 A1 | 5/2011 | Rivera et al. |
| 2011/0124587 A1 | 5/2011 | Jackson et al. |
| 2011/0160311 A1 | 6/2011 | Prakash et al. |
| 2011/0189360 A1 | 8/2011 | Yoo et al. |
| 2011/0195169 A1 | 8/2011 | Markosyan et al. |
| 2012/0164678 A1 | 6/2012 | Stephanopoulos et al. |
| 2012/0214752 A1 | 8/2012 | Markosyan |

FOREIGN PATENT DOCUMENTS

| | | |
|---|---|---|
| CN | 1100727 | 3/1995 |
| CN | 1112565 | 11/1995 |
| CN | 1192447 | 9/1998 |
| CN | 1238341 | 12/1999 |
| CN | 1349997 | 5/2002 |
| CN | 101200480 | 6/2008 |
| JP | 52005800 | 1/1977 |
| JP | 52083731 | 7/1977 |
| JP | 52100500 | 8/1977 |
| JP | 52136200 | 11/1977 |
| JP | 54030199 | 3/1979 |
| JP | 54132599 | 10/1979 |
| JP | 55039731 | 3/1980 |
| JP | 55081567 | 6/1980 |
| JP | 55092400 | 7/1980 |
| JP | 55120770 | 9/1980 |
| JP | 55138372 | 10/1980 |
| JP | 55159770 | 12/1980 |
| JP | 55162953 | 12/1980 |
| JP | 56099768 | 8/1981 |
| JP | 56109568 | 8/1981 |
| JP | 56121453 | 9/1981 |
| JP | 56121454 | 9/1981 |
| JP | 56121455 | 9/1981 |
| JP | 56160962 | 12/1981 |
| JP | 57002656 | 1/1982 |
| JP | 57005663 | 1/1982 |
| JP | 57046998 | 3/1982 |
| JP | 57075992 | 5/1982 |
| JP | 57086264 | 5/1982 |
| JP | 58020170 | 2/1983 |
| JP | 58028246 | 2/1983 |
| JP | 58028247 | 2/1983 |
| JP | 58212759 | 12/1983 |
| JP | 58212760 | 12/1983 |
| JP | 59045848 | 3/1984 |
| JP | 62166861 | 7/1987 |
| JP | 63173531 | 7/1988 |
| JP | 1131191 | 5/1989 |
| JP | 3262458 | 11/1991 |
| JP | 6007108 | 1/1994 |
| JP | 6192283 | 7/1994 |
| JP | 7143860 | 6/1995 |
| JP | 7177862 | 7/1995 |
| JP | 8000214 | 1/1996 |
| JP | 9107913 | 4/1997 |
| JP | 2000236842 | 9/2000 |
| JP | 2002262822 | 9/2002 |
| JP | 2010516764 | 5/2010 |
| KR | 20070067199 | 6/2007 |
| KR | 20080071605 | 8/2008 |
| KR | 20090021386 | 3/2009 |
| RU | 2111969 | 5/1998 |
| RU | 2123267 | 12/1998 |
| RU | 2156083 | 9/2000 |
| RU | 2167544 | 5/2001 |
| RU | 2198548 | 2/2003 |
| WO | 2005089483 | 9/2005 |
| WO | 2006072878 | 7/2006 |
| WO | 2006072879 | 7/2006 |
| WO | 2008091547 | 7/2008 |
| WO | 2009071277 | 6/2009 |
| WO | 2009108680 | 9/2009 |
| WO | 2010118218 | 10/2010 |
| WO | 2011059954 | 5/2011 |
| WO | 2011153378 | 12/2011 |
| WO | 2012082493 | 6/2012 |
| WO | 2012082677 | 6/2012 |
| WO | 2012102769 | 8/2012 |

(56) References Cited

FOREIGN PATENT DOCUMENTS

| WO | 2012108894 | 8/2012 |
|---|---|---|
| WO | 2012109585 | 8/2012 |
| WO | 2013022989 | 2/2013 |

OTHER PUBLICATIONS

"Kitahata, S. et al., ""Production of Rubusoside Derivatives by Transgalactosylation of Various b-Galactosidases""", Agric. Biol. Chem., vol. 53, No. 11 1989, 2923-2928".

"Methanol". Available online from Sigma-Aldrich as of Jan. 4, 2016. pp. 1-2.

"Saponification (Base Hydrolysis) of Organic Materials". Sessions Biogeochemistry Lab. Available as of Jul. 2009 from www.gps.caltech.eduhals/resources/lab_methods/pdf...list/saponification.pdf. pp. 1-2.

"Toxicity, Alcohols". Available online as of Jan. 29, 2010 from emedicine.medscape.com. pp. 1-4.

A-Glucosyltransferase Treated Stevia, Japan's Specifications and Standards for Food Additives, VIII edition, 2009, p. 257.

Ahmed, et al., "Use of p-Bromophenacyl Bromide to Enhance Ultraviolet Detection of Water-Soluble Organic Acids (Steviolbioside and Rebaudioside B) in High-Performance Liquid Chromatographic Analysis", Journal of Chromatography, vol. 192, 1980, 387-393.

Chang, S. S. et al., "Stability Studies of Stevioside and Rebaudioside A in Carbonated Beverages", Journal of Agricultural and Food Chemistry, vol. 31, 1983, 409-412.

Chen, et al., "Enrichment and separation of rebaudioside A from stevia glycosides by a novel adsorbent with pyridyl group", Science in China, vol. 42, No. 3 1999, 277-282.

Chen, et al., "Selectivity of polymer adsorbent in adsorptive separations of stevia diterpene glycisides", Science in China, vol. 41, No. 4 1998, 436-441.

Chen, et al., "Studies on the adsorptive selectivity of the polar resin with carbonyl group on rebaudioside A", Acta Polymeric Scnica, No. 4 1999, 398-403.

Crammer, et al. Progress in the chemistry and properties of rebaudiosides. Development in Sweeteners 3, Elsevier Applied Science, London, Polypeptide. 1987, pp. 45-64. (Year: 1987).

Crammer, et al., "Sweet glycosides from the Stevia plant", Chemistry in Britain, Oct. 1986, 915-916, 918.

Darise et al., "Enzymic Transglucosylation of Rubusoside and the Structure-Sweetness Relationship of Steviol Bisglycosides," Agric. Biol. Chem. vol. 48(10), 1984, 2483-2488.

Dubois et al., "Diterpenoid Sweeteners. Synthesis and Sensory Evaluation of Stevioside Analogues with Improved Organoleptic Properties," J. Med. Chem_ vol. 28, (1985) 93-98.

Fuh, ""Purification of steviosides by membrane and ion exchange process"", Journal of Food Science, vol. 55, No. 5 1990, 1454-1457.

Fukunaga et al., "Enzymic Transglucosylation Products of Stevioside: Separation and Sweetness-evaluation," Agric. Biol_ Chem. vol. 53(6) (1989) 1603-1607.

Fullas et al., "Separation of natural product sweetening agents using overpressured layer chromatography," Journal of Chromatography vol. 464 (1989) 213-219.

Hale, et al., "Amylase of Bacillus Macerans", Cereal Chemistry, vol. 28, No. 1, Jan. 1951, 49-58.

International Search Report and Written Opinion of PCT/US20101055960.

International Search Report and Written Opinion of PCT/US2011/036063, dated Aug. 5, 2011.

International Search Report and Written Opinion of PCT/US2011/047498, dated Dec. 22, 2011.

International Search Report and Written Opinion of PCT/US2011/047499, dated Dec. 22, 2011.

International Search Report and Written Opinion of PCT/US2011/064343.

International Search Report and Written Opinion of PCT/US20111028028.

International Search Report and Written Opinion of PCT/US20111033734.

International Search Report and Written Opinion of PCT/US20111033737.

International Search Report and Written Opinion of PCT/US20111033912.

International Search Report and Written Opinion of PCT/US20111035173.

International Search Report and Written Opinion of PCT/US2012/024585.

International Search Report and Written Opinion of PCT/US2012/024722.

International Search Report and Written Opinion of PCT/US2012/030210.

International Search Report and Written Opinion of PCT/US2012/043294.

International Search Report and Written Opinion of PCT/US2012/051163.

International Search Report and Written Opinion of PCT/US2012/052659.

International Search Report and Written Opinion of PCT/US2012/052665.

International Search Report and Written Opinion of PCT/US20131030439.

Jaitak, et al., "An Efficient Microwave-assisted Extraction Process of Stevioside and Rebaudioside—A from Stevia Rebaudiana (Bertoni)", Phytochem. Anal. vol. 20 2009, 240-245.

Kennelly, "Sweet and non-sweet constituents of Stevia rebaudiana", Stevia: The genus *Stevia*, Taylor & Francis, 2002, 68-85.

Kinghorn, "Overview", Stevia: The genus *Stevia*, Taylor & Francis, 2002, 1-17.

Kobayashi, et al., "Dulcoside A and B, New diterpene glycosides from Stevia Rebaudiana", Phytochemistry, vol. 16 1977, 1405-1408.

Kochikyan, et al., "Combined Enzymatic Modification of Stevioside and Rebaudioside A", Applied Biochemistry and Microbiology, vol. 42, No. 1, 2006, 31-37.

Kohda, et al., "New sweet diterpene glucosides from Stevia Rebaudiana", Phytochemistry, vol. 15 1976, 981-983.

Kovylyaeva, et al., "Glycosides from Stevia rebaudiana", Chemistry of Natural Compounds, vol. 43, No. 1 2007, 81-85.

Liu, et al., "Study of stevioside preparation by membrane separation process", Desalination, vol. 83 1991, 375-382.

Lobov, S. V. et al., "Enzymic Production of Sweet Stevioside Derivatives: Transglucosylation of Glucosidases", Agric. Biol. Chem., vol. 55, No. 12 1991, 2959-2965.

Montovaneli, et al., "The effect of temperature and flow rate on the clarification of the aqueous Stevia-extract in fixed-bed column with zeolites", Brazilian Journal of Chemical Engineering, vol. 21, No. 3 2004, 449-458.

Moraes, et al., "Clarification of Stevia rebaudiana (Bert.) Bertoni extract adsorption in modified zeolites", Acta Scientiarum, vol. 23, No. 6 2001, 1375-1380.

Ohta et al., "Characterization of Novel Steviol Glycosides from Leaves of Stevia rebaudiana Morita," J. Appl. Glycosi., vol. 57, 199-209, 2010.

Ohtani et al. "Chapter 7. Methods to improve the taste of the sweet principles of Stevia rebaudiana." The Genus *Stevia*, edited by A. Douglas Kinghom, CRC Press 2001, Taylor and Francis, London and New York, pp. 138-159.

Phillips, K. C., "Stevia: steps in developing a new sweetener", In T.H. Grenby, Editor, Developments in Sweeteners-3, Elsevier 1987, 1-43.

Pol, et al., "Comparison of two different solvents employed for pressurised fluid extraction of stevioside from Stevia rebaudiana: methanol versus water". Anal Bioanal Chem vol. 388 2007, 1847-1857.

Prakash et al., "Development of rebiana, a natural, non-caloric sweetener," Jul. 1, 2008, Food and Chemical Toxicology, vol. 46, Is. 7, Sup. 1, p. S75-S82.

Recrystallization Technique: Proper purification of crystalline solids. Available online as of Dec. 4, 2009 from www.erowid.org. pp. 1-3.

(56) References Cited

OTHER PUBLICATIONS

Remington: The Science and Practice of Pharmacy, 21st Edition. The University of the Sciences in Philadelphia, 2006. Part 5, p. 700.
Richman et al., "Fuctional genomics uncovers three glucosyltransferases involved in the synthesis of the major sweet glucosides of Stevia rebaudiana," The Plant Journal, vol. 41 (2005) 56-67.
Sakamoto et al., "Application of 13C NMR Spectroscopy to Chemistry of Natural Glycosides: Rebaudioside-C, a New Sweet Diterpene Glycoside of Stevia Rebaudiana", Chem. Pharm. Bull., vol. 25, 1977, 844-846.
Shi, et al., ""Synthesis of bifunctional polymeric adsorbent and its application in purification of Stevia glycosides"", & Functional Polymers, vol. 50 2002, 107-116.
Shibata et al., ""Glucosylation of Steviol and Steviol-Glucosides in Extracts from Stevia rebaudiana Bertoni,"" Plant vol. 95, (1991) 152-156.
Starratt, et al., ""Rebaudioside F, a diterpene glycoside from Stevia Rebaudiana", Phytochemistry, vol. 59 2002 , 367-370".
Sweet Green Fields, LLC, "Notice to the U.S. Food and Drug Administration (FDA) that the use or Rebiana (Rebaudiosid A) derived from Stevia rebaudiana, as a Food Ingredient is Generally Recognized as Safe (GRAS)," Jan. 15, 2009, http:/www.accessdataida.gov/scriptsficn/gras_notices/grn000282.pdf (obtained from the Web on May 8, 2012) entire document esp. p. 22, Table 1.
Tanaka, 0. , "Improvement of taste of natural sweeteners", Pure & Appl. Chem., vol. 69, No. 4 1997, 675-683.
Teo, et al., ""Validation of green-solvent extraction combined with chromatographic chemical fingerprint to evaluate quality of Stevia rebaudiana Bertoni"", J. Sep. Sci, vol. 32 2009, 613-622.
United Nations' Food and Agriculture Organization/Joint Expert Committee on Food Additives (2010) Steviol Glycosides, Compendium of Food Additive Specifications, FAO JECFA Monographs 10, 17-21.
Van der Maarel et al., "Properties and applications of starch-converting enzymes of the a-amylase family," Journal of Biotechnology, vol. 94 (2002) 137-155.
Vasquez, Stimulation of the Gerbil's Gustatory Receptors by Some Potently Sweet Terpenoids, J. Agric. Food Chem., vol. 41, 1305-1310, 1993.
Yamamoto, K. et al., "Effective Production of Glycosyl-steviosides by a-1,6 Transglucosylation of Dextrin Dextranase", Biosci. Biotech. Biochem. vol. 58, No. 9 1994, 1657-1661.
Yoda, et al., "Supercritical fluid extraction from Stevia rebaudiana Bertoni using CO2 and CO2+ water: extraction kinetics and identification of extracted components", Journal of Food Engineering, vol. 57 2003, 125-134.
Zell, et al., "Investigation of Polymorphism in Aspartame and Neotame Using Solid-State NMR Spectroscopy", Tetrahedron, vol. 56, 2000, 6603-6616.
Zhang, et al., "Membrane-based separation scheme for processing sweetener from Stevia leaves", Food Research International, vol. 33 2000, 617-620.
Bruno C. Hancock and Michael Parks. What is the True Solubility Advantage for Amorphous Pharmaceuticals? Pharmaceutical Research, vol. 17, No. 4, 2000. (Year: 2000).
D. M. Parikh ("Achieving Pharmaceutical Solubility Enhancements Using Spray Drying," downloaded Jun. 7, 2020 from https://www.powderbulksolids.com/article/achieving-pharmaceutical-solubility-enhancernents-using-spray-drying). Dated Feb. 1, 2008. (Year: 2008).
Chemical Abstracts, Database accession No. 58543-17-2.
Ohtani K et al, "Further study on the 1,4-alpha-transglucosylation of rubusoside, a sweet steviol-bisglucoside from Rubus suavissimus.", Agric. Biol. Chem., Aug. 8, 1990, pp. 449-453.

\* cited by examiner

Rebaudioside A

Rebaudioside B

REBAUDIOSIDE C

STEVIA COMPOSITION

BACKGROUND OF THE INVENTION

Field of the Invention

The invention relates to a process for producing a highly purified food ingredient from the extract of the *Stevia rebaudiana* Bertoni plant and its use in various food and beverage products.

Description of the Related Art

Nowadays sugar alternatives are receiving increasing attention due to awareness of many diseases in conjunction with consumption of high-sugar foods and beverages. However many artificial sweeteners such as dulcin, sodium cyclamate and saccharin were banned or restricted in some countries due to concerns on their safety. Therefore non-caloric sweeteners of natural origin are becoming increasingly popular. The sweet herb *Stevia rebaudiana* Bertoni produces a number of diterpene glycosides which feature high intensity sweetness and sensory properties superior to those of many other high potency sweeteners.

The above-mentioned sweet glycosides, have a common aglycon, steviol, and differ by the number and type of carbohydrate residues at the C13 and C19 positions. The leaves of *Stevia* are able to accumulate up to 10-20% (on dry weight basis) steviol glycosides. The major glycosides found in *Stevia* leaves are Rebaudioside A (2-10%), stevioside (2-10%), and Rebaudioside C (1-2%). Other glycosides such as Rebaudioside B, D, E, and F, steviolbioside and rubusoside are found at much lower levels (approx. 0-0.2%).

Two major glycosides—stevioside and Rebaudioside A (Reb A), were extensively studied and characterized in terms of their suitability as commercial high intensity sweeteners. Stability studies in carbonated beverages confirmed their heat and pH stability (Chang S. S., Cook, J. M. (1983) Stability studies of stevioside and Rebaudioside A in carbonated beverages. *J. Agric. Food Chem.* 31: 409-412.)

Steviol glycosides differ from each other not only by molecular structure, but also by their taste properties. Usually stevioside is found to be 110-270 times sweeter than sucrose, Rebaudioside A between 150 and 320 times, and Rebaudioside C between 40-60 times sweeter than sucrose. Dulcoside A is 30 times sweeter than sucrose. Rebaudioside A has the least astringent, the least bitter, and the least persistent aftertaste thus possessing the most favorable sensory attributes in major steviol glycosides (Tanaka O. (1987) Improvement of taste of natural sweeteners. *Pure Appl. Chem.* 69:675-683; Phillips K. C. (1989) *Stevia*: steps in developing a new sweetener. In: Grenby T. H. ed. Developments in sweeteners, vol. 3. Elsevier Applied Science, London. 1-43). The chemical structure of Rebaudioside A is shown in FIG. 1.

Methods for the extraction and purification of sweet glycosides from the *Stevia Rebaudiana* plant using water or organic solvents are described in, for example, U.S. Pat. Nos. 4,361,697; 4,082,858; 4,892,938; 5,972,120; 5,962,678; 7,838,044 and 7,862,845.

However, even in a highly purified state, steviol glycosides still possess non-sweet taste attributes such as bitterness, sweet aftertaste, licorice flavor, etc. One of the main obstacles for the successful commercialization of *Stevia* sweeteners are such non-sweet taste attributes. It was shown that these flavor notes become more prominent as the concentration of steviol glycosides increases (Prakash I., DuBois G. E., Clos J. F., Wilkens K. L., Fosdick L. E. (2008) Development of Rebiana, a natural, non-caloric sweetener. Food Chem. Toxicol., 46, S75-S82).

Rebaudioside B (CAS No: 58543-17-2), or Reb B, also known as stevioside $A_4$ (Kennelly E. J. (2002) Constituents of *Stevia rebaudiana* In *Stevia*: The genus *Stevia*, Kinghorn A. D. (Ed), Taylor & Francis, London, p. 71), is one of the sweet glycosides found in *Stevia rebaudiana*. Sensory evaluations show that Reb B was approximately 300-350 times sweeter than sucrose, while for Reb A this value was approximately 350-450 (Crammer, B. and Ikan, R. (1986) Sweet glycosides from the *Stevia* plant. Chemistry in Britain 22, 915-916, and 918). The chemical structure of Rebaudioside B is shown in FIG. 2a.

It was believed that Reb B forms from partial hydrolysis of Rebaudioside A during the extraction process (Kobayashi, M., Horikawa, S., Degrandi, I. H., Ueno, J. and Mitsuhashi, H. (1977) Dulcosides A and B, new diterpene glycosides from *Stevia rebaudiana*. Phytochemistry 16, 1405-1408). However further research shows that Reb B occurs naturally in the leaves of *Stevia rebaudiana* and currently it is one of nine steviol glycosides recognized by FAO/JECFA (United Nations' Food and Agriculture Organization/Joint Expert Committee on Food Additives) in calculating total steviol glycosides' content in commercial steviol glycosides preparations (FAO JECFA (2010) Steviol Glycosides, Compendium of Food Additive Specifications, FAO JECFA Monographs 10, 17-21).

It is also noted that no significant work has been conducted to determine the potential of Reb B as a sweetener or food ingredient. Moreover Reb B is often viewed as process artifact and unnecessary impurity in commercial steviol glycosides preparations. No significant evaluation of Reb B influence on overall taste profile of steviol glycosides preparations has been conducted.

In food and beverage applications, the solubility of high intensity sweeteners like steviol glycosides is very important and can be a significant barrier to achieve the desirable sweetness and taste profile. However highly purified steviol glycosides possess relatively low water solubility. For example Rebaudioside A (Reb A) thermodynamic equilibrium solubility at room temperature is only 0.8%. On the other hand, the water solubility of Reb B is reported to be about 0.1% and that of Reb D (FIG. 2b) is even lower, only at 0.01-0.05% at room temperature (Kinghorn A. D. (2002) Constituents of *Stevia rebaudiana* In *Stevia*: The genus *Stevia*, Kinghorn A. D. (Ed), Taylor & Francis, London, p. 8). Reb B or Reb D can be solubilized at higher concentrations at a higher temperature, but they will quickly crystallize back from solution upon cooling to room temperature. Considering high sweetness intensity of steviol glycosides (100-300 times of sugar sweetness)—even 0.05% solubility may seem sufficient for many applications.

In many food processes where highly concentrated ingredients are used, a highly soluble form of Reb B and Reb D will be necessary.

Considering the facts mentioned above, it is necessary to evaluate Reb B as a sweetener and food ingredient and develop a simple and efficient process for food grade Reb B preparations suitable for food applications.

SUMMARY OF THE INVENTION

In this invention, a process is developed to prepare combinations of different glycosides and food ingredients with Reb B. The process allows to preparation of blends more soluble than a mechanical blend of initial ingredients.

Within the description of this invention we show that, when applied in specific manner, certain blend of Reb B with other steviol glycosides, may impact the taste profile and offer significant advantages for *Stevia* sweeteners' use in various applications.

In an embodiment of the present invention, certain blend of Reb B with Reb A may impact the taste profile and offer significant advantages for *Stevia* sweeteners' use in various applications.

In one embodiment of present invention certain blend of Reb B with Reb D, impacts the taste profile and offer significant advantages for *Stevia* sweeteners' use in various applications.

In another embodiment of present invention we show that, when applied in specific manner, certain blend of Reb B and other steviol glycosides with sweeteners from sugar alcohol group impact the taste profile and offer significant advantages for *Stevia* sweeteners' use in various applications.

In yet another embodiment of present invention we show that, when applied in specific manner, certain blend of Reb B and other steviol glycosides with sweeteners selected from group of natural high intensity sweetener impact the taste profile and offer significant advantages for *Stevia* sweeteners' use in various applications.

In one embodiment of present invention we show that, when applied in specific manner, certain blend of Reb B and other steviol glycosides with compositions selected from glycosylated natural high intensity sweetener group impact the taste profile and offer significant advantages for *Stevia* sweeteners' use in various applications.

In another embodiment of present invention we show that, when applied in specific manner, certain blend of Reb B and other steviol glycosides with sweeteners selected from group of synthetic high intensity sweeteners impact the taste profile and offer significant advantages for *Stevia* sweeteners' use in various applications.

In yet another embodiment of present invention we show that, when applied in specific manner, certain blend of Reb B and other steviol glycosides with ingredients selected from oligosaccharide group impact the taste profile and offer significant advantages for *Stevia* sweeteners' use in various applications.

In one embodiment of present invention we show that, when applied in specific manner, certain blend of Reb B and other steviol glycosides with sweeteners from caloric sweetener group impact the taste profile and offer significant advantages for *Stevia* sweeteners' use in various applications.

Hereinafter the term "steviol glycoside(s)" will mean Rebaudioside A (Reb A), Rebaudioside B (Reb B), Rebaudioside C (Reb C), Rebaudioside D (Reb D), Rebaudioside E (Reb E), Rebaudioside F (Reb F), Stevioside (Stev), Steviolbioside (Sbio), Dulcoside A (Dulc A), Rubusoside (Rub), or other glycoside of steviol and/or combinations thereof.

Hereinafter the terms "total steviol glycosides", or "total glycosides", or "TSG", will mean the sum of concentrations (% wt/wt on anhydrous basis) of Reb A, Reb B, Reb C, Reb D, Reb E, Reb F, Stevioside, Steviolbioside, Dulcoside A, Rubusoside, or other glycosides of steviol.

Hereinafter unless specified otherwise the purity of used Reb A, Reb B, and Reb D, is at least 95% (wt/wt, on anhydrous basis).

Hereinafter the terms "Reb A/B" and "Reb A/Reb B" will mean blends/mixtures of Reb A and Reb B prepared by process of present invention.

Hereinafter, unless specified otherwise the solubility of material is determined in reverse osmosis (RO) water at room temperature. Where the solubility is expressed as "%" it to be understood as number of grams of material soluble in 100 grams of solvent.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention. The drawings illustrate embodiments of the invention and together with the description serve to explain the principles of the embodiments of the invention.

DETAILED DESCRIPTION OF THE INVENTION

Figure 1:
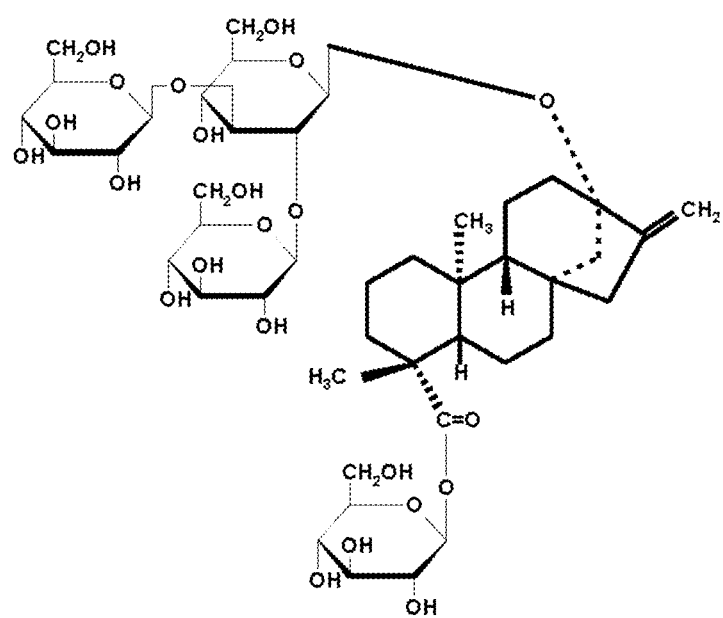
FIG. 1 shows the chemical structure of Reb A.
Figure 2A:
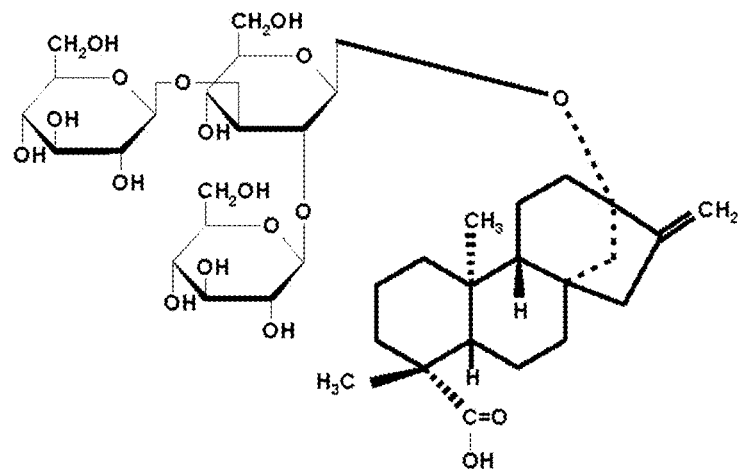
FIGS. 2a and 2b show the chemical structures of Reb B and Reb D, respectively.
Figure 2B:
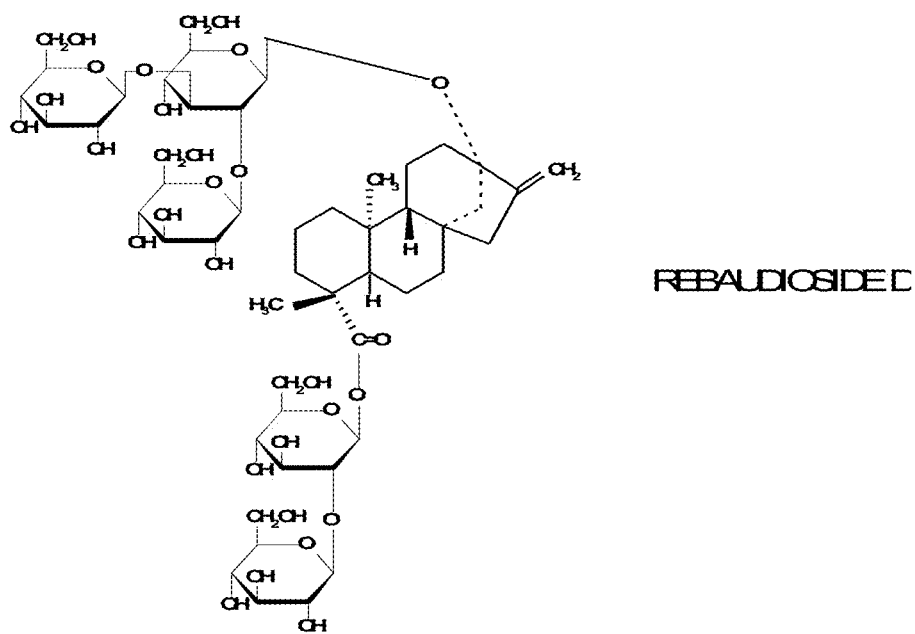

Advantages of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

In one embodiment of invention a process is developed to prepare combinations of different glycosides and food ingredients with Reb B.

In one embodiment the invention describes a sweetened ingestible product comprising blends of Reb B and at least one sweetener, selected from different groups of sweet molecules for producing a blend of sweeteners and use thereof in various food and beverage products as a sweetener and flavor modifier. The groups of sweet molecules comprise and include combinations of the following:

Steviol glycosides and *Stevia* extracts,
Other natural sweeteners (Luo Han Guo extract, Mogrosides, Mogroside V, Glycyrrhizin, Thaumatin, Brazzein, etc),
Glycosylated terpenoid sweeteners (glucosylated steviol glycosides and glucosylated mogrosides, etc)
Synthetic high intensity sweeteners (aspartame, saccharin, sucralose, Acesulfame-K, etc),
Sugar alcohols (erythritol, maltitol, sorbitol, etc),
Oligosaccharides (fructooligosaccharides, inulin, inulooligosaccharides, maltooligosaccharides etc) and Caloric sweeteners (sugar, fructose, dextrose, maltose, lactose, corn syrup, and HFCS etc).

The invention, in part, pertains to an ingredient comprising selected molecules of steviol glycosides (as defined above) of *Stevia rebaudiana* Bertoni plant.

The invention, in part, pertains to ingredients comprising specific blends of steviol glycosides and Reb B, and other steviol glycosides.

The invention, in part, pertains to an ingredient comprising steviol glycosides of *Stevia rebaudiana* Bertoni plant and a sweetener (or combination of sweeteners) from other natural sweeteners including but not limited to, Luo Han Guo extract, Mogrosides, Mogroside V, Glycyrrhizin, Thaumatin, Brazzein, etc.

The invention, in part, pertains to ingredients comprising specific blends of steviol glycosides and Reb B, and a sweetener (or combination of sweeteners) from other natural sweeteners including but not limited to, Luo Han Guo extract, Mogrosides, Mogroside V, Glycyrrhizin, Thaumatin, Brazzein, etc.

The invention, in part, pertains to ingredients comprising steviol glycosides of *Stevia Rebaudiana* Bertoni plant and a composition comprising glycosylated terpenoid sweeteners including but not limited to, glucosylated Steviol Glycosides and glucosylated Mogrosides.

In one embodiment the invention, in part, pertains to ingredients comprising specific blends of steviol glycosides and Reb B, and a composition comprising glycosylated terpenoid sweeteners including but not limited to, Glucosylated Steviol Glycosides and Glucosylated Mogrosides.

The invention, in part, pertains to ingredients comprising steviol glycosides of *Stevia Rebaudiana* Bertoni plant and a sweetener (or combination of sweeteners) from synthetic high intensity sweeteners including but not limited to aspartame, saccharin, sucralose, Acesulfame-K, neotame.

The invention, in part, pertains to ingredients comprising specific blends of steviol glycosides and Reb B, and a sweetener (or combination of sweeteners) from synthetic high intensity sweeteners including but not limited to aspartame, saccharin, sucralose, Acesulfame-K, neotame.

The invention, in part, pertains to an ingredient comprising steviol glycosides of *Stevia rebaudiana* Bertoni plant and a sweetener (or combination of sweeteners) from sugar alcohols including but not limited to erythritol, maltitol, sorbitol, xylitol.

The invention, in part, pertains to ingredients comprising specific blends of steviol glycosides and Reb B, and a sweetener (or combination of sweeteners) from sugar alcohols including but not limited to erythritol, maltitol, sorbitol, xylitol.

The invention, in part, pertains to an ingredient comprising steviol glycosides of *Stevia rebaudiana* Bertoni plant and a sweetener (or combination of sweeteners) from oligosaccharides including but not limited to fructo-oligosaccharides, inulin, inulo-oligosaccharides, polydextrose, and malto-oligosaccharides.

The invention, in part, pertains to ingredients comprising specific blends of steviol glycosides and Reb B, and a sweetener (or combination of sweeteners) from oligosaccharides including but not limited to fructo-oligosaccharides, inulin, inulo-oligosaccharides, polydextrose, and malto-oligosaccharides.

The invention, in part, pertains to an ingredient comprising steviol glycosides of *Stevia rebaudiana* Bertoni plant and a sweetener (or combination of sweeteners) from caloric sweeteners group including but not limited to sugar, invert-sugar, fructose, dextrose, maltose, lactose, corn syrup, and HFCS.

The invention, in part, pertains to ingredients comprising specific blends of steviol glycosides and Reb B, and a sweetener (or combination of sweeteners) from caloric sweeteners group including but not limited to sugar, invert-sugar, fructose, dextrose, maltose, lactose, corn syrup, and HFCS.

In another aspect, a sweetened ingestible product comprising a) at least one sweetener, selected from the group consisting of: steviol glycosides, other natural sweeteners, glycosylated terpenoid sweeteners, synthetic high intensity sweeteners, sugar alcohols, oligosaccharides, caloric sweeteners, and a combination thereof, wherein said at least one sweetener or sweetener combination is present in the product at a concentration above 2% sucrose equivalent sweetness, and b) Reb B at a concentration from 10 to 300 ppm.

In another aspect, the invention is also directed to a method for producing a soluble sweetener composition, comprising the steps of providing low solubility *Stevia* sweeteners, solubilizing them in water under gradient temperature treatment conditions, to produce highly stable concentrated solution, and spray drying the highly stable concentrated solution to obtain a highly soluble *Stevia* composition.

In one embodiment of this invention the initial materials for preparing soluble sweetener composition were selected from the group including Reb D, Reb A, Reb B, and steviolbioside (Sbio).

In another aspect of this invention, steviol glycosides compositions with lower solubility, (lower than 1%) were combined with Reb B through the method described above, and yielded compositions with significantly higher solubility (more than 1%). This phenomenon was unexpected, as pure Reb B on its own has <0.1% solubility.

The compositions of present invention can be used as sweetness enhancer, flavor enhancer and sweetener in various food and beverage products. Non-limiting examples of food and beverage products include carbonated soft drinks, ready to drink beverages, energy drinks, isotonic drinks, low-calorie drinks, zero-calorie drinks, sports drinks, teas, fruit and vegetable juices, juice drinks, flavored water, dairy drinks, yoghurt drinks, alcohol beverages, powdered beverages, bakery products, bread, cookies, biscuits, muffins, rolls, baking mixes, cereals, breakfast cereals confectioneries, candies, toffees, chewing gum, frostings, dairy products, flavored milk, yoghurts, flavored yoghurts, cultured milk, frozen dairy desserts including ice cream, sauces and gravies, soy sauce and other soy base products, salad dressings, mayonnaise, vinegar, condiments and relishes, meat products, fish-meat products, bottled and canned foods, frozen-desserts, jams and jellies, gelatins, puddings and fillings tabletop sweeteners, processed fruits and vegetables.

Additionally the compositions can be used in drug or pharmaceutical preparations and cosmetics, including but not limited to toothpaste, mouthwash, cough syrup, chewable tablets, lozenges, vitamin preparations, and the like.

The compositions can be used "as-is" or in combination with other sweeteners, flavors and food ingredients.

Non-limiting examples of sweeteners include steviol glycosides, stevioside, Rebaudioside A, Rebaudioside B, Rebaudioside C, Rebaudioside D, Rebaudioside E, Rebaudioside F, dulcoside A, steviolbioside, rubusoside, as well as other steviol glycosides found in *Stevia rebaudiana* Bertoni plant and mixtures thereof, *Stevia* extract, Luo Han Guo extract, mogrosides, high-fructose corn syrup, corn syrup, invert sugar, fructooligosaccharides, inulin, inulooligosaccharides, coupling sugar, maltooligosaccharides, maltodextins, corn syrup solids, glucose, maltose, sucrose, lactose, aspartame, saccharin, sucralose, sugar alcohols.

Non-limiting examples of flavors include lemon, orange, fruit, banana, grape, pear, pineapple, bitter almond, cola, cinnamon, sugar, cotton candy, vanilla flavors.

Non-limiting examples of other food ingredients include flavors, acidulants, organic and amino acids, coloring agents, bulking agents, modified starches, gums, texturizers, preservatives, antioxidants, emulsifiers, stabilizers, thickeners, gelling agents.

The following examples illustrate various embodiments of the invention. It will be understood that the invention is not limited to the materials, proportions, conditions and procedures set forth in the examples, which are only illustrative.

Example 1

Preparation of Reb D and Reb B Soluble Composition 70 g of rebaudioside D with 98.1% purity (dry weight basis), having water solubility of 0.03% and 30 g of rebaudioside B with 99.0% purity (dry weight basis), and having water solubility of 0.01%, both produced by PureCircle Sdn Bhd (Malaysia), were mixed with 400 g water and incubated in thermostatted oil bath. The temperature was increased at 1° C. per minute to 121° C. The mixture was maintained at 121° C. for 1 hour and then the temperature was decreased to 80° C., at 1° C. per minute, and the obtained solution was spray dried using YC-015 laboratory spray drier (Shanghai Pilotech Instrument & Equipment Co. Ltd., China) operating at 175° C. inlet and 100° C. outlet temperature. Solution was maintained at 80° C. to prevent premature crystallization. About 90 g of amorphous powder was obtained with 1% solubility.

Example 2

Effect of *Stevia* Composition on Solubility in Water

Solubility were evaluated for Reb A, Reb B, mechanical blends of Reb A and Reb B powders of different ratios, and mixtures of Reb A and Reb B prepared according to process described in EXAMPLE 1. Reb A and Reb B showed solubility around 1% and 0.1% at room temperature and increased solubility on heating to a higher temperature. Table 1 shows the solubility of different ingredients and their blends.

TABLE 1

| Solubility in water | Pure Reb A | Pure Reb B | Reb A/Reb B blends (wt/wt ratio of Reb B to total glycosides) | | | | | |
|---|---|---|---|---|---|---|---|---|
| | | | Mechanical blend | | | Blend made by process of invention | | |
| | | | 10% | 16% | 26% | 10% | 16% | 26% |
| 0.5% | Yes | No* | No* | No* | No* | Yes | Yes | Yes |
| 1% | Yes | No* | No* | No* | No* | Yes | Yes | Yes |
| 2% | No | No* | No* | No* | No* | Yes | Yes | Yes |
| 5% | No | No* | No* | No* | No* | Yes | Yes | Yes |

*Suspension was opaque and particles settled down when mixing was stopped

Example 3

Sweetness Factor (SF) Determination

The sweetness factors for different sweetener from all major groups were measured by tasting several concentrations of each sweetener in water by trained panel. From the sensory test at a, the concentration (%) that corresponds to the 5% sucrose equivalent (SE) sweetness were estimated and listed in Table 2. The sweetness equivalent (SE) of high intensity sweeteners (HIS) varies according to the target sugar equivalent sweetness levels, that are tested as shown in Table 3. Table 3 also shows the sweetness factors of Reb A, Reb B and a test sample (Reb A/B) with a blend of Reb A and Reb B at 84:16 ratio.

TABLE 2

Sweetness factors of selected sweeteners

| Sweetener Group | Sweetener | Usage Level, % | Calculated SF |
|---|---|---|---|
| Steviol Glycoside | Reb A (97%) | 0.0172 | 291 |
| | Reb D (97%) | 0.0172 | 291 |
| | Reb B (98%) | 0.0397 | 126 |
| Other Natural HIS | Mogroside V (70%) | 0.0212 | 236 |
| Glycosylated Terpenoid sweetener | Glucosylated Steviol Glycosides | 0.0556 | 90 |
| Synthetic HIS | Sucralose | 0.0083 | 602 |
| Sugar Alcohol | Erythritol | 7.49 | 0.67 |
| | Maltitol | 6.44 | 0.77 |
| Oligosaccharide | FOS (Frutalose L90) | 21 | 0.24 |
| Caloric Sweetener | Sugar | 5 | 1 |

TABLE 3

Sweetness factor of selected steviol glycosides

| SE levels | 2.5% | 5.0% | 7.5% | 10.0% |
|---|---|---|---|---|
| Reb A | 400 | 290 | 250 | 200 |
| Reb B | 146 | 126 | 95 | 59 |
| Reb A/B | 350 | 260 | 220 | 190 |

Example 4

Effect of *Stevia* Composition on Sweetness Profile in Water

Figure 3:
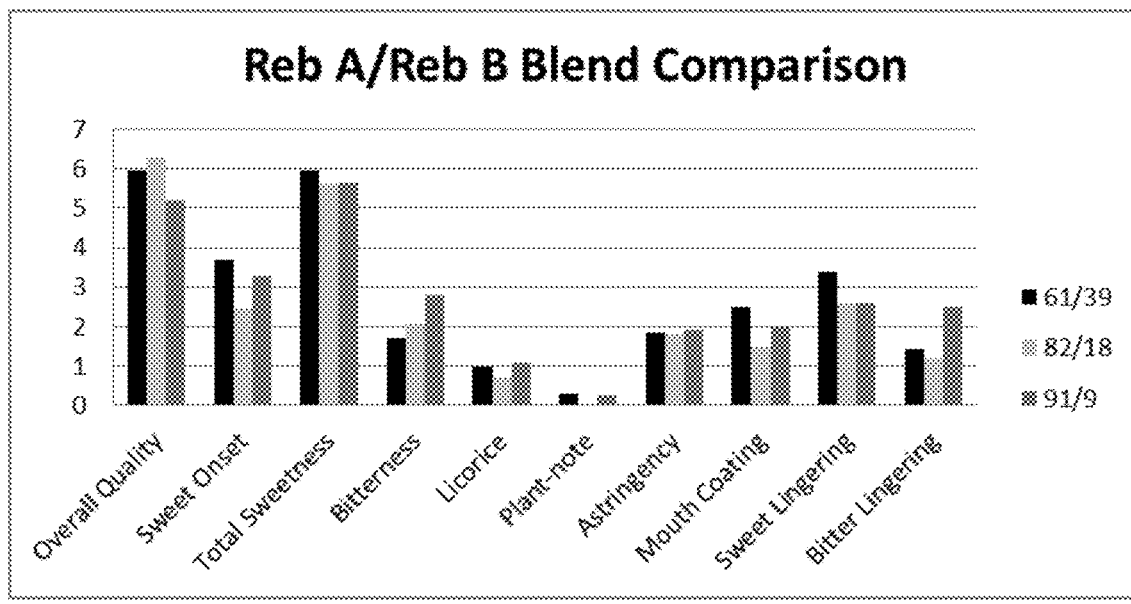
FIG. 3 shows the sweetness profile of compositions featuring different ratios of Reb A to Reb B (Reb A/Reb B).

In another embodiment, *Stevia* sweetener (Reb A, Reb B or blends thereof) solutions were made by completely dissolving *Stevia* into distilled water. Solutions were tasted and evaluated by a trained panel. FIG. 3 shows the effect of different ratio of Reb A and Reb B on sweetness profile and associated aftertastes (vertical axis is a relative intensity of different attributes). All solutions were made with different mass ratio of Reb A and Reb B as shown in FIG. 3 to get the 7% sweetness equivalent. Reb B a mount varied between 20 mg/kg to 150 mg/kg. It is apparent that the blend of Reb A and Reb B show unexpectedly improved sweetness profile at certain ratios.

Example 5

In one embodiment, Reb B was combined (at 50, 150 and 300 ppm) with several sweeteners listed in Table 2 to make solutions in plain water. Some of the sweeteners were tested at two different concentrations to obtain around 2% sugar equivalent sweetness without any Reb B. A trained panel conducted sensory tests to determine the effect of the addition of different amounts of Reb B to each sweetener on overall sweetness quality and intensity as shown in Table 4. In presence of Reb B, most of the sweeteners showed a surprising level of enhancement of sweetness intensity. The addition of Reb B generally increased upfront sweetness, made the sweetness profile rounded and contributed to sweetness lingering at a higher level.

TABLE 4

Sugar equivalent sweetness (%) for different sweetener combinations

| | SE of Sweetener/Reb B combination | | | |
|---|---|---|---|---|
| Sweetener | 0 ppm Reb B | 50 ppm Reb B | 150 ppm Reb B | 300 ppm Reb B |
| Mogroside V (100 ppm) | 2.5 | 4 | 5.5 | 8-8.5 |
| Mogroside V (212 ppm) | 5.5-6 | 7 | 9 | 10-10.5 |
| Sucralose (40 ppm) | 2-2.5 | 5 | 7.5-8 | 11 |
| Sucralose 83 ppm | 5 | 7 | 11 | 14 |
| Erythritol (3.5%) | 1-1.5 | 3 | 5.5-6 | 9 |
| Erythritol (5.0%) | 3 | 4 | 8 | 9.5 |
| Maltitol (6.44%) | 5 | 6 | 9 | 12 |
| FOS (21%) | 5 | 6.5 | 8 | 11 |

Example 6

In one embodiment, several concentrations of the Reb A/B blend (used in EXAMPLE 3) were tested to match the sweetness of Reb B solutions at 50, 150 and 300 ppm. A trained panel of 13 members found that 22, 68 and 128 ppm of Reb A/B matched the sweetness intensity of Reb B solutions with 50, 150 and 300 ppm concentrations respectively. Table 5 shows the combination of different sweeteners that were used for different applications to show the effect of Reb B and Reb A/B on the sweetness and flavor profile in different applications.

All sensory attributes were rated by trained panelists on a scale of zero (0) to ten (10). Samples were presented in a randomized fashion and labeled with three-digit codes.

Sweet Onset—This attribute describes the time at which panelists perceived sweetness upon placing the sample in the mouth. A score of zero indicates immediate identification of sweetness, whereas a score of ten indicates a long delay in the time that sweetness was perceived.

Total Sweetness—This attribute describes the highest intensity of sweetness perceived during tasting. A score of zero indicates no sweetness, while a score of ten indicates very high sweetness.

Bitterness—This attribute describes the highest intensity of bitterness perceived during tasting. A score of zero indicates no bitterness, while a score of ten indicates very high bitterness.

Rounded Sweetness—This attribute describes the duration of sweetness while samples are in the mouth. A score of zero indicates that the sweetness comes and goes very quickly and is more like high intensity sweeteners in its temporal profile, while a score of ten indicates that the sweetness lasts for a long time, and is more similar to sugar in its temporal profile.

Flavor Intensity—This attribute describes the highest intensity of flavor perceived during tasting. A score of zero indicates no flavor, while a score of ten indicates very high flavor.

Astringency—This attribute describes the highest intensity of astringency perceived during tasting. A score of zero indicates no astringency, while a score of ten indicates very high astringency.

Mouth Coating—This attribute describes the highest intensity of sweetness coating perceived while samples are in the mouth. A score of zero indicates that there is no coating of sweetness, while a score of ten indicates very high sweetness coating.

Sweet Lingering—This attribute describes the highest intensity of sweetness perceived after the sample has been swallowed. A score of zero indicates that there is no sweetness perceived after the sample has been swallowed, while a score of ten indicates high sweetness after the sample has been swallowed.

Bitter Lingering—This attribute describes the highest intensity of bitterness perceived after the sample has been swallowed. A score of zero indicates that there is no bitterness perceived after the sample has been swallowed, while a score of ten indicates high bitterness after the sample has been swallowed.

Aftertaste Mouth Coating—This attribute describes the highest intensity of sweetness coating perceived after the sample has been swallowed. A score of zero indicates that there is no sweetness coating perceived after the sample has been swallowed, while a score of ten indicates high sweetness coating after the sample has been swallowed.

Tartness—This attribute describes the highest intensity of tartness perceived during tasting. A score of zero indicates no tartness, while a score of ten indicates very high tartness.

Cooling Sensation—This attribute describes the highest intensity of cooling sensation perceived during tasting. A score of zero indicates no cooling sensation, while a score of ten indicates very high cooling sensation. The consideration of these attributes was used for selecting different sweetener combinations for application examples.

TABLE 5

Sweetener combination tested for applications

| Sweetener | Sweetener + Reb B | Sweetener + Reb A/B |
|---|---|---|
| Erythritol 5% | +50 ppm | +22 ppm |
| Sucralose 40 ppm | +150 ppm | +68 ppm |
| Mogroside V 100 pm | +300 ppm | +128 ppm |
| Maltitol (6.44%) | +50 ppm | +22 ppm |
| FOS (21%) | +150 ppm | +68 ppm |

Example 7

Figure 4:
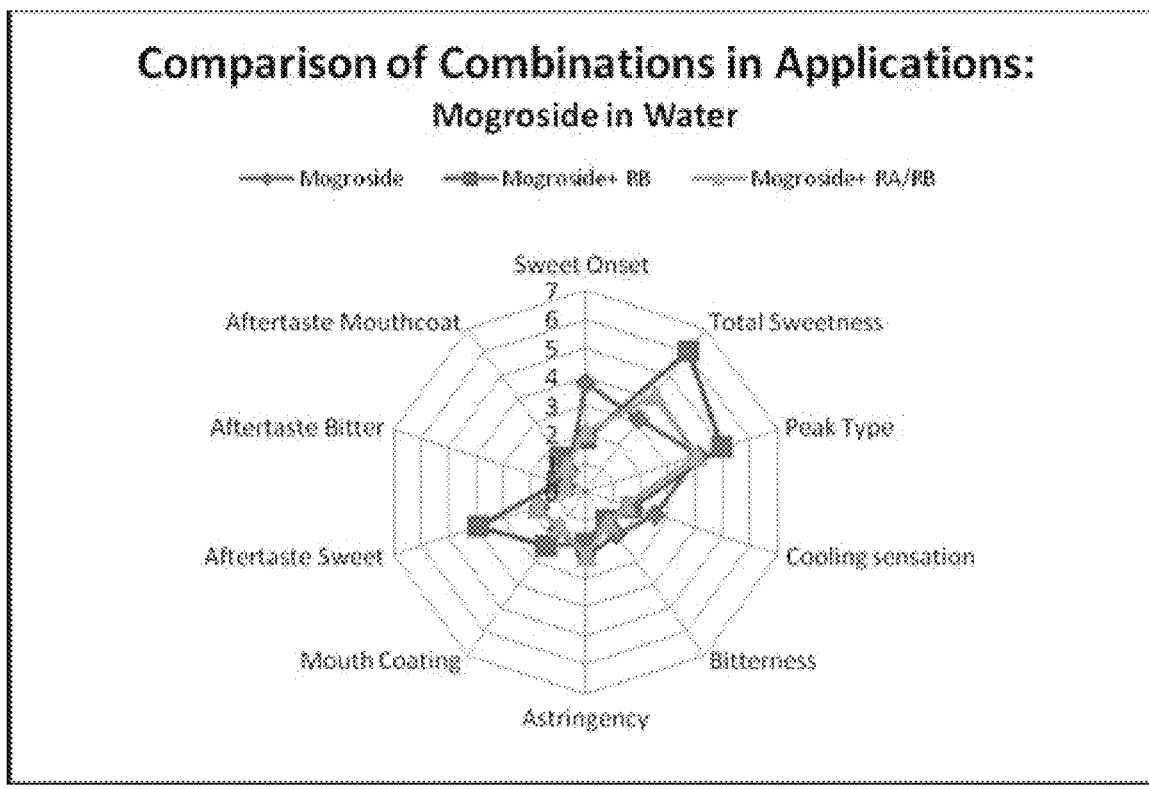
FIG. 4 shows the effect of Reb B and a blend of steviol glycosides on sweetness profile of Mogroside in water.

Water solution of mogroside (100 ppm) sweetener was tested against solutions made with mogroside (100 ppm)+Reb B (300 ppm) and mogroside (100 ppm)+Reb A/B (Example 3) blend (128 ppm) by a 13 members trained panel. They found Reb B with mogroside sample increases sweetness level significantly, improves the onset of sweetness and decreases the bitterness. In presence of Reb A/B blend and mogroside, the increase in sweetness is higher than mogroside solution, but lower than mogroside+Reb B solution. FIG. 4 shows the difference in taste attributes for all three sweetener systems.

Example 8

Figure 5A:
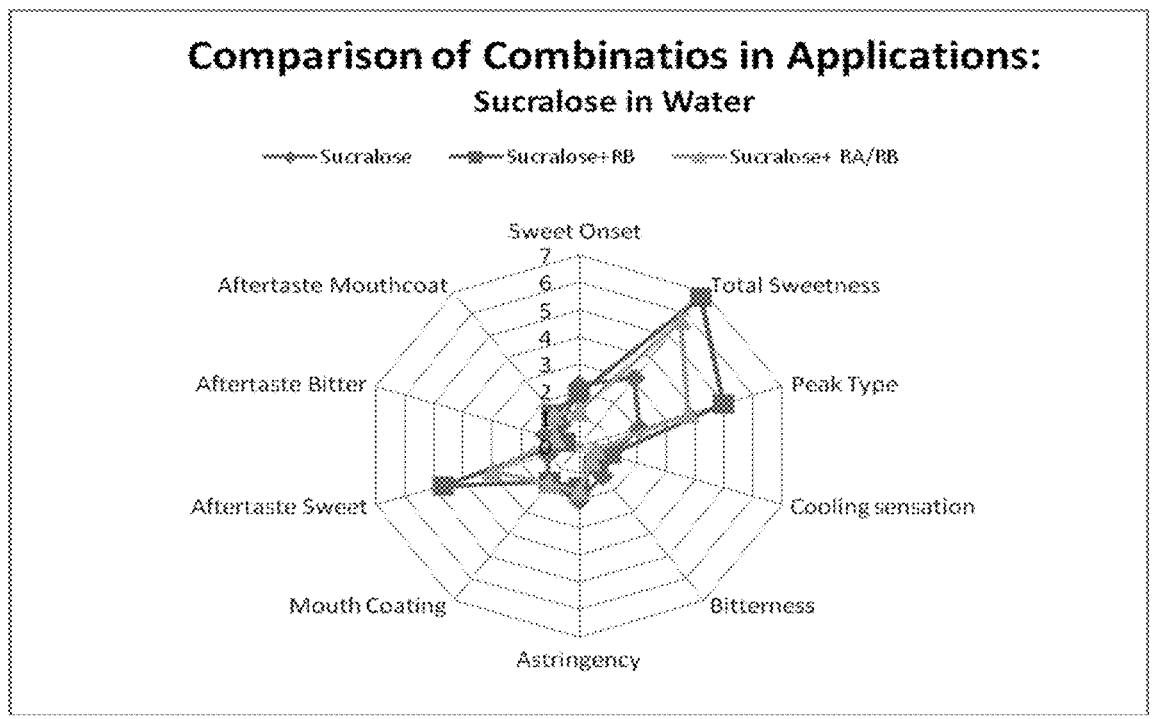
FIGS. 5a and 5b show the effect of Reb B and a blend of steviol glycosides on sweetness profile of Sucralose in water and in a flavored drink.

Water solution of sucralose (40 ppm) was tested against solutions made with sucralose (40 ppm)+Reb B (150 ppm) and sucralose (40 ppm)+Reb A/Reb B (Example 3) blend (68 ppm) by a 13 members trained panel. They found Reb B with sucralose sample had significantly higher sweetness level. Reb B improved the onset of sweetness and decreased the off taste slightly. In presence of Reb A/Reb B blend and sucralose, the increase in sweetness is higher than sucralose solution, but lower than sucralose+Reb B solution. FIG. 5a shows the difference in taste attributes for all three sweetener systems containing sucralose and steviol glycosides.

Example 9

Figure 5B:
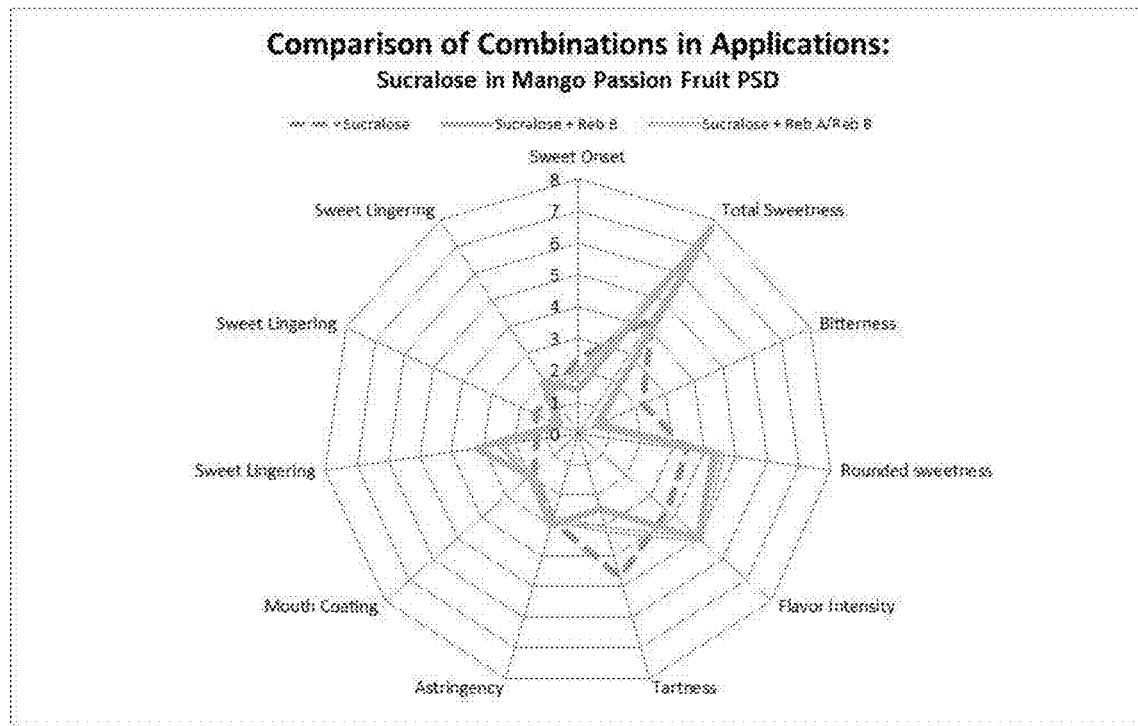

The sucralose sweetener and the steviol glycosides compositions (described in EXAMPLE 8) were used for making a mango-passion fruit flavored Powder Soft Drink (PSD) and a sensory panel found the soft drink containing sucralose with steviol glycosides significantly increased the sweetness, enhanced the fruit flavor, reduced the astringency, and made the drink more rounded in sweetness and acid profile. FIG. 5b shows the impact of different sweetener system on the taste attributes of the beverage.

Example 10

Figure 6A:
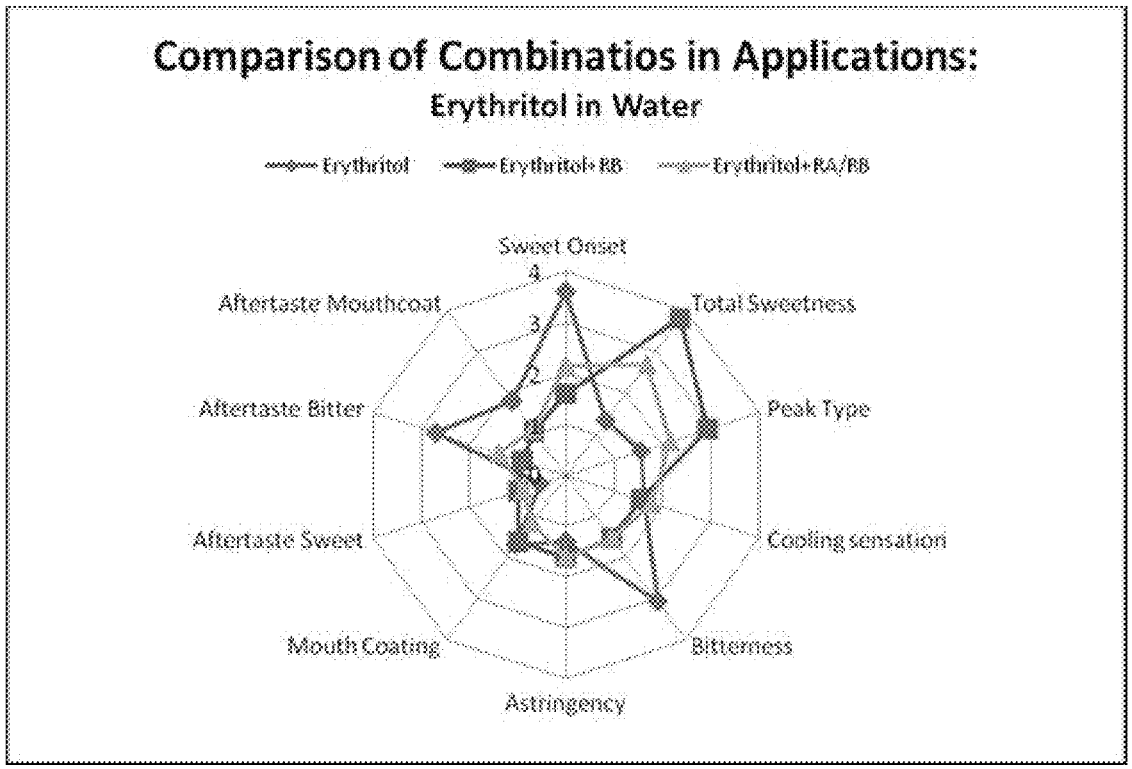
FIGS. 6a and 6b show the effect of Reb B and a blend of steviol glycosides on sweetness profile of Erythritol in water and in a flavored drink.

Water solution of erythritol (5%) was tested against solutions made with erythritol (5%)+Reb B (50 ppm) and erythritol (5%)+Reb A/Reb B (Example 3) blend (22 ppm) by a 13 members trained panel. They found Reb B improved the taste of erythritol sample significantly by increasing the sweetness and reducing the bitterness and cooling effect. Along with higher sweetness level, Reb B improved the onset of sweetness and the peak sweetness without increasing the sweetness lingering (sweet after taste). In presence of Reb A/Reb B blend and erythritol, the solution had a higher sweetness and showed fairly similar improvement of other attributes as Reb B showed with erythritol. FIG. 6a shows the difference in taste attributes for all three sweetener systems containing sucralose and steviol glycosides.

Example 11

Figure 6B:
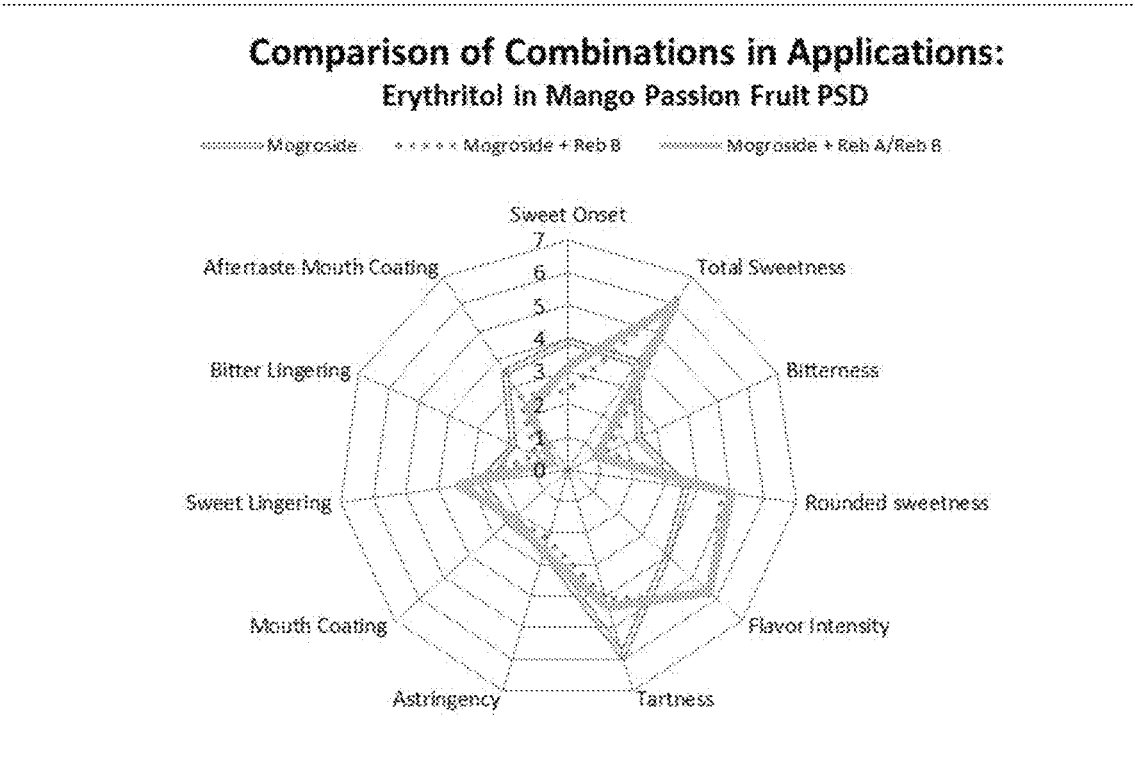

The erythritol sweetener and the steviol glycosides compositions (described in EXAMPLE 10) were used for making a mango-passion fruit flavored Powder Soft Drink (PSD) and a sensory panel found the soft drink containing erythritol with steviol glycosides significantly increased the sweetness, reduced the bitterness, enhanced the fruit flavor, reduced the astringency, and made the drink more rounded in sweetness and acid profile. Steviol glycosides also reduced the aftertaste. FIG. 6b shows the impact of different sweetener system containing erythritol on the taste attributes of the beverage.

Example 12

Figure 7A:
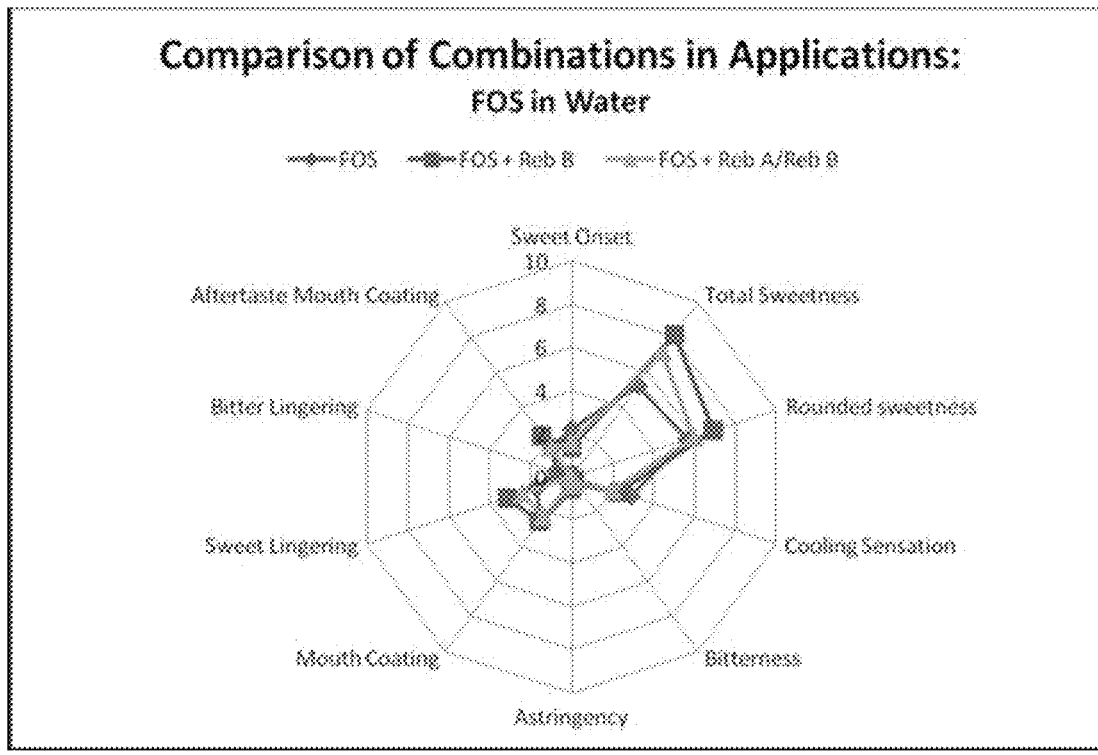
FIGS. 7a and 7b show the effect of Reb B and a blend of steviol glycosides on sweetness profile of FOS or Fructooligosaccharide in water and in an alcoholic beverage.

Fructo-oligosaccharide or FOS solution (21%) was tested against solutions made with FOS (21%)+Reb B (150 ppm) and FOS (21%)+Reb A/Reb B (Example 3) blend (68 ppm) by a 13 members trained panel. They found Reb B with FOS sample had significantly higher sweetness and made the sweetness profile rounded. In presence of Reb A/Reb B blend and FOS, the increase in sweetness is higher than FOS solution but lower than sucralose+Reb B solution. FIG. 7a shows the difference in taste attributes for all three sweetener systems containing FOS and steviol glycosides.

Example 13

Figure 7B:
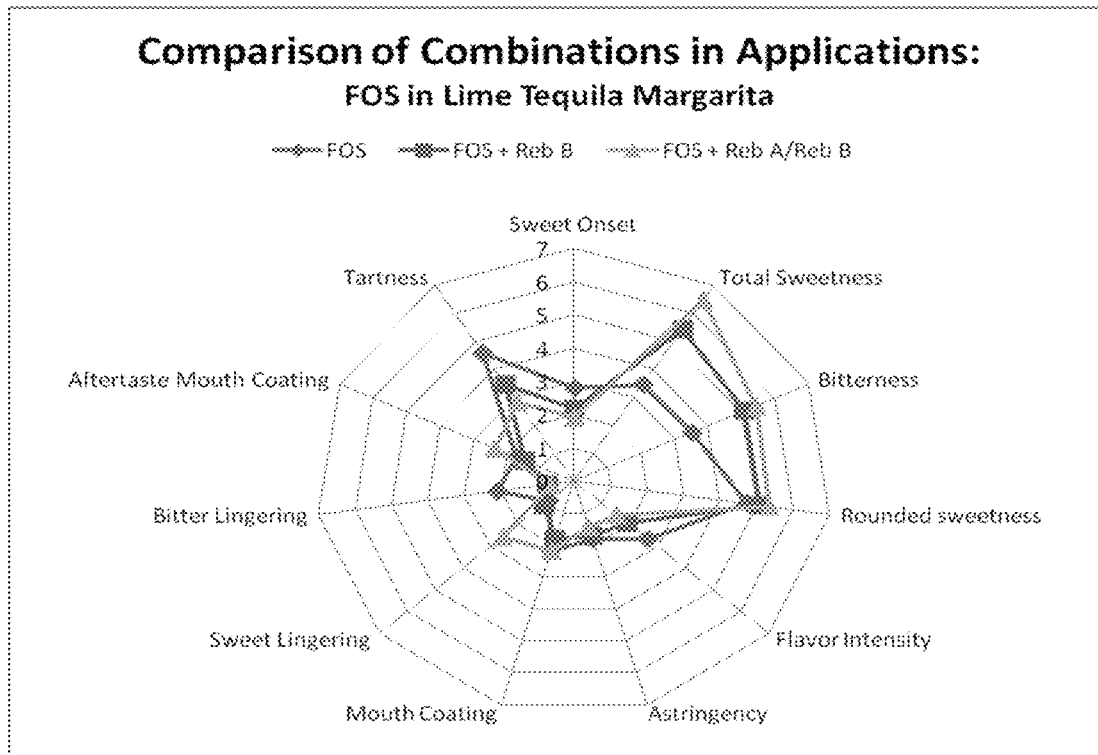

The Fructo-oligosaccharide (FOS) sweetener and the steviol glycosides compositions (described in EXAMPLE 12) were used for making an alcoholic beverage—lime-tequila margarita drink using Margarita pre-mix from FIS (Flavor International Systems), recommended usage was 0.4%. Prepared Lime Tequila Margarita blank containing about 10% alcohol, no sugar added. To sweeten the beverage, used FOS (21%), FOS+Reb B (150 ppm), and FOS+Reb A/Reb B (68 ppm). Descriptive Sensory evaluation was conducted with 8-13 panelists. Sensory results showed that, with the addition of Reb B, there was enhancement in the sweetness profile of the alcoholic beverage product. The sweetness onset was earlier in the profile, and there was an increase in total sweetness and the sweetness profile was more rounded. There was a decrease in flavor intensity, bitter lingering, and tartness. FIG. 7b shows the impact of different sweetener system on the taste attributes of the beverage.

Example 14

Effect of Reb B on No Fat (NF) Yogurt

Samples were prepared according to formulas outlined below in Table 6. Samples included a full sugar reference, an aspartame reference, a Reb A control and several test samples with a Reb A/Reb B blends. The samples were evaluated by a trained panel and screened for overall sweetness, bitterness, astringency, mouth coating, flavor intensity, acidity/tartness, sweet lingering and bitter lingering. Reb A had bitterness at the end that was not present in samples with Reb A/Reb B blends. Both Reb A and blends enhanced the acidity of the yogurt. A significant improvement of taste was found with the blend of Reb B/Reb A, where Reb B ratio to total glycosides (TSG) ranged between 0.5 to 50%, more specifically 10% to 40% of Reb B to total glycosides.

TABLE 6

|  | Control | 1 | 2 | 3 | 4 | 5 |
|---|---|---|---|---|---|---|
| NF Yogurt (%) | 92 | 99.96 | 99.94 | 99.93 | 99.94 | 99.94 |
| Sugar (%) | 8 |  |  |  |  |  |
| Aspartame (%) |  | 0.0400 |  |  |  |  |
| Reb A (%) |  |  | 0.0250 |  | 0.0250 | 0.0250 |
| NSF02 (natural flavor) (%) |  |  | 0.0350 | 0.0350 | 0.0350 | 0.0350 |
| Reb B (%) |  |  |  | 0.0056 | 0.0140 | 0.0090 |
| Reb B/TSG (%) | 0 | 0 | 0 | 16% | 36% | 26% |

Example 15

Chocolate Milk

A series of samples were prepared to having sugar-equivalent sweetness around 5.5%. The control sample was sweetened with 5.5% sugar the test samples were sweetened with different ratios of Reb A/Reb as shown in Table 7 below. The samples were evaluated by a trained panel and screened for overall sweetness, bitterness, astringency, mouth coating, flavor intensity, acidity/tartness, sweet lingering and bitter lingering. Pure Reb A had separate peaks for sweetness, dairy notes, and cocoa notes. The test samples had a very balanced and more rounded sweetness profile with an increasing amount of Reb B content in the sweetener as outlined in the following table. A significant improvement of taste was found with the blend of Reb A/Reb B. where Reb B to total glycosides ratio ranged between 0.5 to 50, more specifically 10 to 400 of Reb B to total glycosides.

TABLE 7

| Ingredient, % | Control | Sample # 1 | 2 | 3 | 4 | 5 | 6 |
|---|---|---|---|---|---|---|---|
| Low-fat milk or Skim milk | 94.00 | 99.48 | 99.47 | 98.47 | 99.47 | 99.46 | 99.45 |
| Sugar | 5.50 | | | | | | |
| Cocoa Powder | 0.50 | 0.50 | 0.50 | 1.50 | 0.50 | 0.50 | 0.50 |
| Reb A | | 0.0242 | 0.0242 | 0.0242 | 0.0169 | 0.0121 | |
| Reb B | | | 0.0046 | 0.0060 | 0.0157 | 0.0262 | 0.0524 |
| Carrageenan | | 0.0160 | 0.0160 | 0.0160 | 0.0160 | 0.0160 | 0.0160 |
| Total | 100 | 100.0 | 100.0 | 100.0 | 100.0 | 100.0 | 100.0 |
| Reb B/TSG ratio | | 0% | 16% | 20% | 48% | 68% | 100% |

Example 16

Table Top Sweeteners

Several table top formulations were developed using different bulking agents, as examples sugar, fructose, dextrose, maltodextrin, polyols, fibers (inulin, Fibersol-2) etc. Table 8 lists a few examples of the formulation with different ratio of Reb B to total glycosides and dextrose as the bulking agent. Each sample of 1 g wt. was developed for providing sweetness equivalent to 8-9 grams of sugar. Each sample was tested in coffee by 11 panel members and screened for sweetness, coffee flavors, bitterness, overall mouthfeel, and residual (lingering) sweetness and bitterness. As the ratio of Reb B to total steviol glycosides increased the overall taste and preference increased. A significant improvement of overall sweetness and mouthfeel was found with the blend of Reb A/Reb B, where Reb B to total glycosides ranged between 1 to 40%, more specifically 7% to 30% of Reb B to total glycosides.

TABLE 8

| | Control | Sample 1 | Sample 2 | Sample 3 |
|---|---|---|---|---|
| Reb A (g) | 0.0400 | 0.0336 | 0.0300 | |
| Reb B (g) | | 0.0064 | 0.0100 | 0.0500 |
| Dextrose (g) | 0.9600 | 0.9560 | 0.9600 | 0.9500 |
| Reb B/TSG (%) | 0 | 16 | 25 | 100 |

Example 17

Baked Goods

The texture and taste profile of baked goods improved with the blend of Reb B and Reb A. Several samples were developed with different ratios of Reb B and Reb A or SG95 (a steviol glycoside product available from PureCircle Inc.); some examples are shown in the Table 9. The samples were evaluated by a trained internal panel and screened for overall sweetness, texture, mouthfeel, mouth coating, flavor intensity, sweet lingering and bitter lingering. The test sample had a better balance of sweetness and overall acceptability. A significant improvement of overall sweetness and mouthfeel was found with the blend of Reb B and Reb A or SG95, where Reb B to total glycosides ranged from 0.5% to 40%, more specifically 7% to 30% of Reb B to total glycosides.

TABLE 9

| Ingredients (%) | Control | Sample 1 | Sample 2 | Sample 3 |
|---|---|---|---|---|
| All-purpose flour | 24.42 | 17.629 | 17.629 | 17.629 |
| Sugar | 23.14 | 12.372 | 12.372 | 12.372 |
| Whole wheat flour | | 5.8763 | 5.8763 | 5.8763 |
| Maltodextrin | | 2.1368 | 2.1368 | 2.1368 |
| Fibersol-2 | | 1.0684 | 1.0684 | 1.0684 |
| Modified starch | | 1.0684 | 1.0684 | 1.0684 |
| Poppy seeds | 1 | 1.0684 | 1.0684 | 1.0684 |
| Baking powder | 0.48 | 1.0684 | 1.0684 | 1.0684 |
| Lemon flavor | 0.83 | 0.886 | 0.886 | 0.886 |
| Salt | 0.71 | 0.7479 | 0.7479 | 0.7479 |
| Baking soda | | 0.3205 | 0.3205 | 0.3205 |
| NSF-02 (Natural flavor) | | 0.0635 | 0.0635 | 0.0635 |
| Reb B | | | 0.025 | 0.02 |
| SG95 | | 0.0302 | | 0.0302 |
| Reb A | | | 0.005 | 0.01 |
| Wet Ingredients | | | | |
| Milk, (2% fat) | 23.99 | 27.244 | 27.244 | 27.244 |
| Soybean oil | 14.78 | 11.753 | 11.753 | 11.753 |
| Eggs | 9.54 | 8.5473 | 8.5473 | 8.5473 |
| Water | | 5.342 | 5.342 | 5.342 |
| Yogurt, Plain non-fat | | 1.6026 | 1.6026 | 1.6026 |
| Lemon juice | 0.59 | 0.641 | 0.641 | 0.641 |
| Vanilla extract | 0.52 | 0.5342 | 0.5342 | 0.5342 |
| Total | 100 | 100 | 100 | 100 |
| Reb B/TSG (%) | 0 | 0 | 16 | 33 |

Example 18

Black Tea with Peach Flavor

The control tea sample had 7.7% sugar content. The test formulas (Table 10) were modified to reduce 70%/a sugar with Reb A or Reb A/B blend (Example 3). The samples were evaluated by a trained panel and screened for overall sweetness, sweet onset, mouthfeel, flavor intensity, bitterness, sweet lingering and bitter lingering. Among the test samples, the sample with Reb A/Reb B had a better balance of sweetness, overall acceptability, earlier onset of sweetness and sugar-like taste profile.

TABLE 10

| Ingredient (%) | Control | Reb A/B | Reb A |
|---|---|---|---|
| Water | 91.849 | 97.2715 | 97.27498 |
| Sugar | 7.7000 | 2.2500 | 2.2500 |
| Black Tea | 0.2750 | 0.2750 | 0.2750 |
| Sodium Citrate | 0.0550 | 0.0550 | 0.0550 |
| Citric Acid | 0.0440 | | |
| Ascorbic Acid | 0.0440 | 0.0440 | 0.0440 |

TABLE 10-continued

| Ingredient (%) | Control | Reb A/B | Reb A |
|---|---|---|---|
| Peach Flavor | 0.0330 | 0.0330 | 0.0330 |
| Xanthan Gum | | 0.0035 | 0.0035 |
| Malic Acid | | 0.0440 | 0.0440 |
| Reb A/B | | 0.0240 | |
| Reb A | | | 0.0205 |
| TOTAL | 100 | 100 | 100 |

Example 19

No-Sugar Added 50% Orange Juice Drink

The juice drinks were made with sugar, Reb A/Reb B (Example 3) blend, and Reb A (steviol glycosides) as shown in the Table 11 below. All samples had a pH around 3.75. The samples were evaluated by a trained panel and screened for overall sweetness, sweet onset, mouthfeel, flavor intensity, bitterness, sweet lingering and bitter lingering. The sample with Reb A/Reb B was less bitter, more tart, more fresh orange flavor, less astringent and less bitter lingering than that with Reb A. Reb A/Reb B was perceived as significantly closer to control in overall flavor profile than Reb A formula.

TABLE 11

| Ingredient (%) | Control-Sugar | Reb A/B | Reb A |
|---|---|---|---|
| Water | 43.9400 | 49.9075 | 49.9160 |
| Orange Juice | 50.0000 | 50.0000 | 50.0000 |
| Sugar | 6.0000 | | |
| Steviol Glycosides | | 0.0225 | 0.0215 |
| Flavor | 0.0400 | 0.0700 | 0.0825 |
| Citric Acid | 0.0200 | | |
| TOTAL | 100 | 100 | 100 |

Example 20

Lemon-Lime Carbonated Soft Drink

The control carbonated soft drink sample was made with high fructose corn syrup (HFCS) 42 and other test samples were made with a combination of HFCS and Reb A/B (Example 3) blend or Reb A to attain 30% less calorie (Table 12). The samples were evaluated by a trained panel and screened for overall sweetness, sweet onset, mouthfeel, flavor intensity, bitterness, sweet lingering and bitter lingering. Product with Reb A/B feels smoother in mouth and is identified as closer to control than Reb A formula. It has less of a sharp sweetness peak than Reb A and reduced terpene notes compared to Reb A. The overall flavor is less altered compared to Reb A.

TABLE 12

| Ingredient (%) | Control | Reb A/B | Reb A |
|---|---|---|---|
| Water | 84.85 | 89.30 | 89.30 |
| HFCS 42 | 14.83 | 10.38 | 10.38 |
| Reb A | | | 0.0049 |
| Reb A/B | | 0.0058 | |
| Xanthan gum | | 0.0050 | 0.0050 |
| Sodium Benzoate | 0.0263 | 0.0263 | 0.0263 |
| Potassium Citrate | 0.0263 | 0.0263 | 0.0263 |
| Citric Acid | 0.1500 | 0.1433 | 0.1433 |

TABLE 12-continued

| Ingredient (%) | Control | Reb A/B | Reb A |
|---|---|---|---|
| Malic Acid | | 0.0050 | 0.0050 |
| Flavor | 0.1110 | 0.1110 | 0.1110 |

Example 21

Peppermint Mouthwash

A commercial unsweetened (no sugar or sweetener) peppermint mouthwash product (Brand: The Natural Dentist) was used to determine the effect of Reb B with other sweetener, as example maltitol, a sugar alcohol on the sensory profile of mouthwash. Mouthwash samples were sweetened with Maltitol (6.44%), Maltitol+Reb B (50 ppm), Maltitol+Reb B (150 ppm). Descriptive sensory evaluation was conducted with 8 panelists. They evaluated several attributes including sweet onset, total sweetness, bitterness, rounded sweetness, flavor intensity, astringency, mouth coating, sweet lingering, bitter lingering, aftertaste mouth coating, tartness. Sensory results showed that the addition of Reb B created an earlier sweetness onset, and higher total sweetness. All other attributes were generally unchanged.

Although the invention and its advantages have been described in detail, it should be understood that various changes, substitutions and alterations can be made herein without departing from the spirit and scope of the invention as defined by the appended claims. Moreover, the scope of the application is not intended to be limited to the particular embodiments of the invention described in the specification. As one skilled in the art will readily appreciate from the disclosure of the invention, the compositions, processes, methods and steps, presently existing or later to be developed that perform substantially the same function or achieve substantially the same result as the corresponding embodiments described herein are encompassed by the scope of the invention.

We claim:

1. A sweet ingestible composition comprising Rebaudioside B and at least one sweetener, selected from the group consisting of Mogroside V, sucralose, erythritol, maltitol, fructooligosaccharides (FOS) and combinations thereof, wherein said at least one sweetener is present in the composition at a concentration above 2% sucrose equivalent sweetness, and Rebaudioside B is present at a concentration from 50 to 300 ppm.

2. A food or beverage product having sweetness, enhanced sweetness, enhanced flavor, or a combination thereof, comprising the sweet ingestible composition of claim 1.

3. A drug, pharmaceutical or cosmetic preparation comprising the sweet ingestible composition of claim 1.

4. A sweetener comprising the sweet ingestible composition of claim 1.

5. The sweet ingestible composition of claim 1, further comprising a flavoring agent.

6. The sweet ingestible composition of claim 1, further comprising a food ingredient selected from the group consisting of acidulants, organic and amino acids, coloring agents, bulking agents, modified starches, gums, texturizers, preservatives, antioxidants, emulsifiers, stabilizers, thickeners, gelling agents, and combinations thereof.

* * * * *